United States Patent [19]

Hsia et al.

[11] Patent Number: 5,599,342

[45] Date of Patent: Feb. 4, 1997

[54] METHOD FOR TREATING PIGMENTATION ABNORMALITIES USING PULSED LASER RADIATION WITH AN ELONGATED CROSS-SECTION AND APPARATUS FOR PROVIDING SAME

[75] Inventors: James C. Hsia, Andover; Robert Schlier, Concord, both of Mass.

[73] Assignee: Candela Laser Corporation, Wayland, Mass.

[21] Appl. No.: 379,776

[22] Filed: Jan. 27, 1995

[51] Int. Cl.$^6$ .......................................... A61N 5/06
[52] U.S. Cl. .................................................. 606/9
[58] Field of Search ..................... 606/10, 11, 12, 606/9, 17, 15, 16; 607/88, 89

[56] References Cited

U.S. PATENT DOCUMENTS

| | | | |
|---|---|---|---|
| 4,718,416 | 1/1988 | Nanaumi. | |
| 4,733,660 | 3/1988 | Itzkan | 128/303 |
| 4,973,848 | 11/1990 | Kolobanov et al. | 250/458 |
| 5,057,104 | 10/1991 | Chess | 606/9 |
| 5,139,495 | 8/1992 | Daikuzono | 606/17 |
| 5,152,759 | 10/1992 | Parel et al. | 606/5 |
| 5,217,455 | 6/1993 | Tan | 606/9 |
| 5,261,904 | 11/1993 | Baker et al. | 606/17 |
| 5,282,797 | 2/1994 | Chess | 606/9 |
| 5,290,273 | 3/1994 | Tan | 606/9 |
| 5,312,395 | 5/1994 | Tan et al. | 606/9 |
| 5,344,418 | 9/1994 | Ghaffari | 606/9 |
| 5,397,327 | 3/1995 | Koop et al. | 606/17 |

FOREIGN PATENT DOCUMENTS

| | | |
|---|---|---|
| 3837248A1 | 5/1990 | Germany. |
| WO91/13653 | 9/1991 | WIPO. |
| WO91/13652 | 9/1991 | WIPO. |

*Primary Examiner*—Angela D. Sykes
*Assistant Examiner*—Sonja Harris-Ogugua
*Attorney, Agent, or Firm*—Testa, Hurwitz & Thibeault, LLP

[57] ABSTRACT

A method for treating pigmentation abnormalities in human skin involves the use of a beam of laser radiation having an elongated cross-sectional area. The beam of pulsed laser radiation having an elongated cross-section is produced using a pulsed laser and a delivery system. An elongated area on the skin including a pigmentation abnormality is irradiated with the laser beam. The laser pulse parameters are tailored to the specific type of pigmentation abnormality (e.g., vascular lesions or tattoos) being treated. The beam may have a cross-sectional area characterized by an aspect ratio of greater than two. Also, the beam may have an elliptical cross-sectional area.

14 Claims, 2 Drawing Sheets

5,599,342

METHOD FOR TREATING PIGMENTATION ABNORMALITIES USING PULSED LASER RADIATION WITH AN ELONGATED CROSS-SECTION AND APPARATUS FOR PROVIDING SAME

FIELD OF INVENTION

This invention relates generally to the treatment of pigmentation abnormalities using lasers. In particular, the invention relates to a method for treating pigmentation abnormalities in human skin using a beam of pulsed laser radiation having an elongated cross-section and an apparatus for providing such beam.

BACKGROUND

Abnormal pigmentation of the skin is commonly seen in dermatologic practice. A subject's skin may have pigmentation abnormalities due to vascular lesions, pigmented lesions, or tattoos. Vascular lesions, such as port wine stain birthmarks, telangiectasia and hemangiomas, are characterized by abnormally enlarged blood vessels. Pigmented lesions are non-vascular disfigurements of the skin caused by an abnormally high concentration of melanin in localized areas of the skin. Such pigmented lesions include freckles, age or liver spots, café au lait birthmarks, lentigines, nevi, melanomes, nevus of Ota and lentigo maligna. Tattoos may be divided into two categories, including self-inflicted tattoos and traumatic tattoos. Traumatic tattoos are created during an accident which causes a scrape or abrasion such that a foreign material becomes imbedded in the skin.

Pulsed laser systems, such as those manufactured by Candela Laser Corporation, have been widely used by plastic surgeons and dermatologists to successfully treat pigmentation abnormalities on the face and other areas of the human body for obvious cosmetic reasons. For example, Candela's Pigmented Lesion Laser has been used to lighten or remove pigmented lesions. Candela's TATULAZR has been used to remove blue/black tattoos. Candela's Vascular Lesion Laser has been used to lighten or remove vascular lesions.

These and other such laser systems typically include a pulsed laser and a delivery system. The delivery system includes a handpiece that delivers pulses of laser radiation to a subject' skin typically having a circular cross-section ranging from 1–10 mm in spot diameter. The treatment procedure generally involves irradiating an area of a subject's skin including a pigmentation abnormality with a beam of pulsed laser radiation.

Undesirable side effects of laser treatment include purpura, hypopigmentation and hyperpigmentation. Purpura is generally attributed to the damage to the skin's microvasculature which results in the treated area of the subject's skin turning blue/black in appearance. Purpura can take up to two weeks to clear and is particularly bothersome when the treated area is on a subject's face. Hyperpigmentation can be caused by the deposition of hemosiderin, a blood breakdown by-product in the skin, which occurs due to damage to the blood vessels. This can result in the treated area of the subject's skin turning brown some days after the treatment and is particularly common when the vessels treated are on the legs. Hyperpigmentation is slow to clear, sometimes taking up to a year to go away. Hypopigmentation is attributable to damage to the melanin-producing cell in the skin. Hypopigmentation is generally transient, but is cosmetically undesirable while it persists.

In treating a pigmentation abnormality which is distinct and clearly demarcated, it is advantageous to irradiate the area of the skin including the abnormality while minimizing exposure of the adjacent normally pigmented tissue to radiation. This results in reduced purpura, hypopigmentation and hyperpigmentation. One technique used involves manipulating the handpiece to trace out or scan the area of the skin including the pigmentation abnormality with the laser pulses having a circular cross-sectional area or spot. In cases where the pigmentation abnormality is elongated in shape, to minimize the exposure of adjacent normally pigmented skin, a pulsed beam with a smaller cross-sectional area is used on the area of the skin including the abnormality. It has been found clinically that using pulses with a small cross-sectional area (spot diameter of 3 mm or less) results in much less purpura and reduced incidence of hypopigmentation and hyperpigmentation.

One problem with this technique, however, is that treatment is quite tedious, since only a small portion of the targeted pigmentation abnormality is irradiated for each laser pulse. Thus, the number of pulses required to treat a pigmentation abnormality and the treatment time increase significantly.

SUMMARY OF THE INVENTION

The present invention features a method for treating pigmentation abnormalities in human skin using a beam of pulsed laser radiation having an elongated cross-sectional area. A beam of pulsed laser radiation having an elongated cross-sectional area is produced using a pulsed laser and a delivery system. An elongated area on the skin including a pigmentation abnormality is irradiated with pulses of laser radiation from the beam. As such, large sections of the abnormality may be irradiated with minimal exposure to adjacent normally pigmented tissue.

The laser pulse parameters are tailored to the specific type of pigmentation abnormality being treated. For treatment of vascular lesions a beam of, laser pulses of at least one hundred microseconds in duration and one-tenth joule are provided by the laser. For treatment of tattoos, a beam of laser pulses of less than five hundred nanoseconds in duration and of at least one-tenth joule are provided by the laser. In one embodiment, the laser beam has a cross-sectional area characterized by an aspect ratio of greater than two. In another embodiment, the laser beam has an elliptical cross-sectional area. The elliptical beam may have a major axis of between about 5–15 mm in length and a minor axis of between about 1–3 mm in length.

The invention also features an apparatus for use with a dermatology laser to treat pigmentation abnormalities in human skin. The apparatus includes a handpiece and a fiber. The fiber connects to the laser for providing a beam of pulsed of laser radiation therefrom. The handpiece, in which the beam of pulsed laser radiation provided by the fiber are converted into an output beam of pulsed laser radiation having an elongated cross-sectional area, is coupled to the fiber. The handpiece is holdable by a user to irradiate an elongated area of the subject's skin including the pigmentation abnormality with pulses of laser radiation from the output beam.

The invention offers numerous advantages over existing dermatologic procedures and devices. One advantage is that larger sections of the pigmentation abnormality can be irradiated, thereby reducing both the number of pulses required to treat the abnormality and the treatment time.

Another advantage is that the invention is energy efficient. That is, for a given amount of laser pulse energy, a longer section of the pigmentation abnormality is treated because much less of the energy is wasted on normally pigmented tissue. Another advantage is exposure to adjacent normally pigmented tissue is reduced, resulting in less purpura, hypopigmentation and hyperpigmentation. Yet another advantage of the invention is that a pigmentation abnormality is more effectively destroyed because longer sections of the abnormality are treated in a single pulse. It has been found clinically that when a large circular diameter beam is used to treat a pigmentation abnormality, the pigmentation abnormality is more effectively cleared than when a small circular beam is used at the same fluence. The use of an elongated beam gives the effectiveness of a large circular beam, while minimizing exposure to adjacent normally pigmented tissue.

BRIEF DESCRIPTION OF THE DRAWINGS

The foregoing and other objects, features and advantages of the invention will become apparent from the following more particular description of preferred embodiments of the invention, as illustrated in the accompanying drawings. The drawings are not necessarily to scale, emphasis instead being placed on illustrating the principles of the present invention.

DETAILED DESCRIPTION

Figure 1:
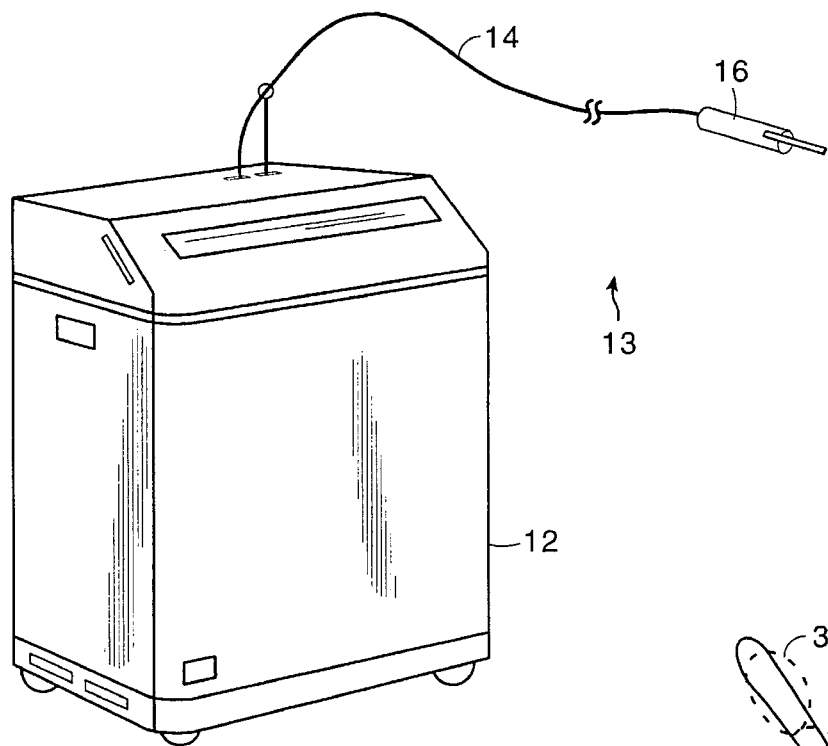
FIG. 1 is an illustration of an apparatus including a laser and a delivery system for practicing invention.

FIG. 1 is an illustration of a flashlamp pumped tunable dye laser system 10 for practicing the invention. The system includes a dye laser 12 and a delivery system 13. While a dye laser is described herein, any other suitable pulsed laser may be used without departing from the scope of the invention. A beam of pulsed laser radiation generated by the laser are directed to a target area of a subject's skin including a pigmentation abnormality via the delivery system.

Figure 2:
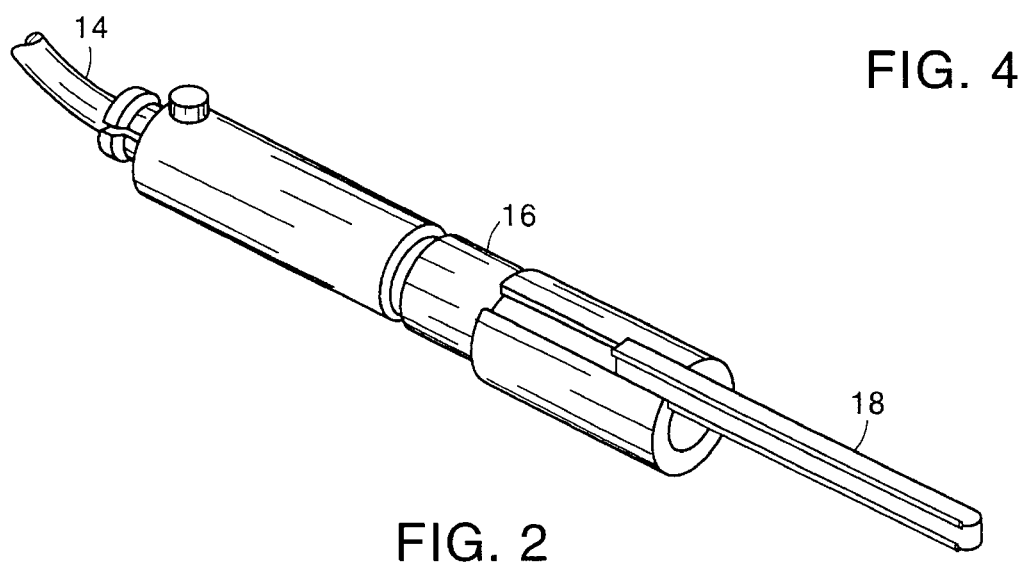
FIG. 2 is an enlarged perspective view of a delivery system incorporating the principles of the invention.

FIG. 2 is an enlarged perspective view of a delivery system incorporating the principles of the invention. The delivery system 13 includes a fiber 14 having a circular cross-section and a handpiece 16. A beam of pulsed laser radiation having a circular cross-section are delivered by the fiber to the handpiece. In accordance with the invention, the beam of laser pulses is converted by the delivery system into a pulsed output beam of laser radiation having an elongated cross-sectional area. To accomplish this, the handpiece may comprise an optical system 20 (FIG. 3) which performs the conversion process. The optical system projects the output beam to an elongated spot adjacent the end of a positioning extension 18. A user holding the handpiece irradiates an elongated area of the subject's skin including the pigmentation abnormality with output pulses from the beam.

Figure 3:
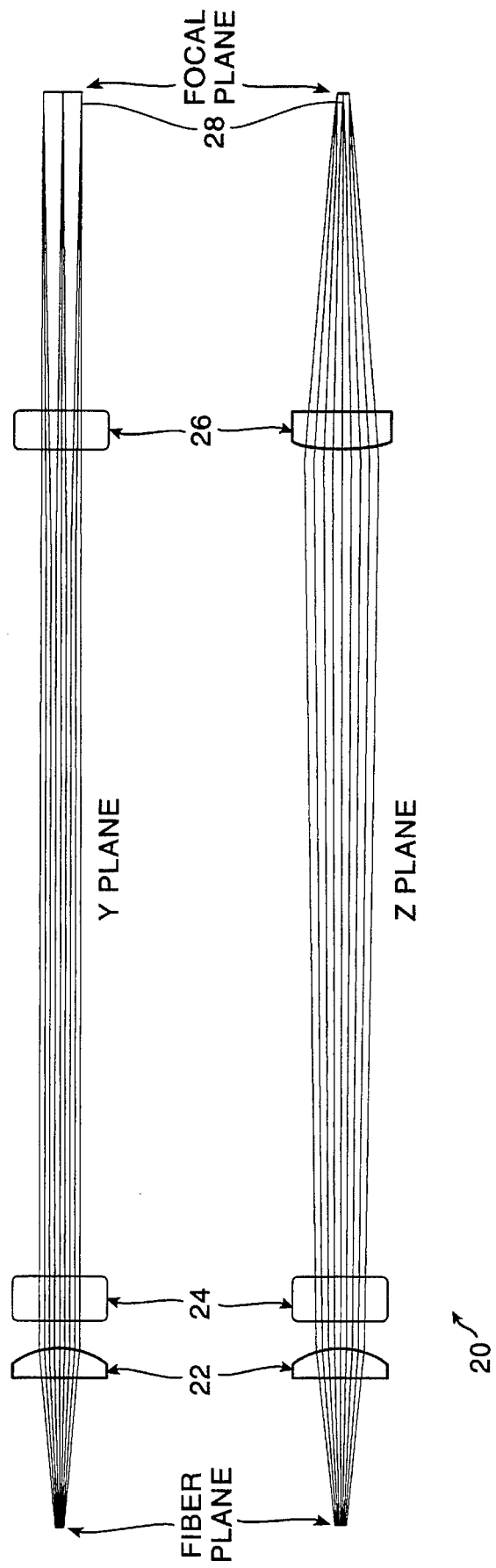
FIG. 3 is an illustration of an optical system useable in the delivery system of FIG. 2.

FIG. 3 is a representative optical system 20 useable in the handpiece shown in two planes (i.e., the Y and Z planes). As shown, the system includes a plano convex spherical lens 22 and two plane convex cylindrical lenses 24, 26 of focal lengths $f_1$, $f_2$, $f_3$ respectively. The Y and Z planes are two mutually perpendicular planes, both perpendicular to the optic axis. The lens 24 is arranged so that its axis of curvature is located in the Z plane, and the lens 26 is arranged so that its axis of curvature is in the Y plane. The lens 22 collimates pulsed laser radiation delivered by the fiber into a cylindrically symmetric pulsed output beam 28. The lens 24 focuses the beam in the Y plane onto the focal plane and has no effect in the Z plane. Conversely, the lens 26 focuses the beam in the Z plane onto the focal plane and has no effect in the Y plane. The optical system shown converts a pulsed input beam from a fiber with a circular cross-section into a pulsed output beam having an elliptical cross-section with a major axis of about 5–15 mm in length and a minor axis of about 1–3 mm in length.

While an optical system comprising three lenses has been described, it is noted that other optical elements may be used without departing from the scope of the invention. For example, the optical system may include two orthogonal cylindrical lenses, highly astigmatic lenses, tilted spherical lenses, anamorphic prisms, or multifaceted prisms. Alternatively, laser pulses may be directly converted by the fiber into output pulses having an elongated cross-section. To accomplish this, the fiber or at least that portion of the fiber disposed in the handpiece has an elongated cross-section. The fiber may have an elliptical cross-section characterized by a ratio of major axis/minor axis, or aspect ratio, or more than two.

Figure 4:
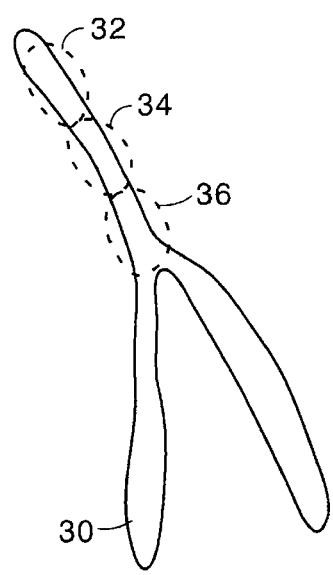
FIG. 4 is an illustration of pigmentation abnormality exposed to a plurality of laser pulses from a beam having an elongated cross-sectional area.

FIG. 4 illustrates the treatment of a pigmentation abnormality 30 in accordance with the invention. The pigmentation abnormality shown may be a vascular lesion or a tattoo. Accordingly, the laser parameters are tailored to the type of pigmentation abnormality being treated. Laser pulses of at least one hundred microseconds in duration and one-tenth joule are provided by the laser to treat vascular lesions. Laser pulses of less than five hundred nanoseconds in duration and of at least one-tenth joule are provided to treat tattoos.

Laser pulses having an elongated cross-section are produced using the laser and delivery system shown in FIG. 1. The laser pulses may have a cross-sectional area characterized by an aspect ratio of greater than two. Further, the pulses may have an elliptical cross-section. Such elliptical spot has a major axis of between about 5–15 mm in length and a minor axis of between about 1–3 mm in length. In any case, an elongated area 32 on the subject's skin including a portion of the pigmentation abnormality is irradiated with laser pulses exiting from the handpiece. The process is repeated for other elongated areas 34, 36 and continues until the entire abnormality has been irradiated. For each area of the subject's skin, the laser pulses are aligned with an elongated portion of the pigmentation abnormality such that large sections of the abnormality are irradiated with minimal exposure to adjacent normally pigmented tissue.

Treatment of pigmentation abnormalities using the method and apparatus of the invention: (1) reduces the number of pulses required to treat the abnormality and the treatment time, (2) is energy efficient in that for a given amount of pulse energy, a longer section of the pigmentation abnormality and proportionately smaller section of normally pigmented tissue are treated, (3) reduces purpura, hypopigmentation and hyperpigmentation by minimizing exposure to adjacent normally pigmented tissue, and (4) more effectively destroys pigmentation abnormalities because longer sections of the abnormality are treated with a single pulse.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims.

We claim:

1. A dermatological method of treating a pigmentation abnormality in human skin comprising:

producing a beam of pulsed laser radiation having an elongated cross-sectional area using a pulsed laser and a delivery system;

irradiating an elongated area on the skin including the pigmentation abnormality with the beam of pulsed laser radiation without cutting said skin.

2. The method of claim 1 further comprising producing a beam of pulsed laser radiation having an aspect ratio of greater than two.

3. The method of claim 1 further comprising producing a beam of pulsed laser radiation having an elliptical cross-sectional area.

4. The method of claim 1 wherein the beam of pulsed laser radiation has an elliptical cross-sectional area with a major axis of between about 5–15 mm in length and a minor axis of between about 1–3 mm in length.

5. The method of claim 1 wherein the delivery system comprises at least one lens for producing a beam of pulsed laser radiation having an elongated cross-sectional area.

6. The method of claim 1 wherein the delivery system comprises a fiber with an elongated cross-section for producing a beam of pulsed of laser radiation having an elongated cross-sectional area.

7. The method of claim 1 further comprising producing a beam of pulsed laser radiation of at least one-tenth joule in energy.

8. The method of claim 1 wherein the pigmentation abnormality is a vascular lesion.

9. A dermatological method of treating a vascular lesion in human skin comprising:

producing a beam of pulsed laser radiation of at least one hundred microseconds in duration and at least one-tenth joule in energy using a pulsed laser and delivery system, the beam of pulsed laser radiation having an elongated cross-sectional area and an aspect ratio greater than two;

irradiating an elongated area of the skin that includes the vascular lesion with the pulsed beam of laser radiation without cutting said skin.

10. The method of claim 9 further comprising producing a beam of pulsed laser radiation having an elliptical cross-sectional area.

11. The method of claim 9 wherein the beam of pulsed of laser radiation has an elliptical cross-sectional area with a major axis of about 5–15 mm in length and a minor axis of about 1–3 mm in length.

12. A dermatological method of treating a tattoo in human skin comprising:

producing a beam of pulsed laser radiation less than five hundred nanoseconds in duration and at least one-tenth joule in energy using a pulsed laser and delivery system, the beam of pulsed laser radiation having an elongated cross-sectional area and an aspect ratio greater than two;

irradiating an elongated area of the skin that includes the tattoo with the pulsed laser radiation without cutting said skin.

13. The method of claim 12 further comprising producing the beam of pulsed laser radiation having an elliptical cross-sectional area.

14. The method of claim 12 wherein the the beam of pulsed of laser radiation has an elliptical cross-sectional area with a major axis of about 5–15 mm in length and a minor axis of about 1–3 mm in length.

* * * * *